United States Patent [19]
Berger-Neel et al.

[11] Patent Number: 4,931,446
[45] Date of Patent: Jun. 5, 1990

[54] ANTIMICROBIAL FOR IN-VITRO DIAGNOSTIC KITS

[75] Inventors: Bonnie Berger-Neel, Wildwood; Beth K. Gershon, Lake Zurich; John P. Groff, Gurnee, all of Ill.

[73] Assignee: Abbott Laboratories, Abbott Park, Ill.

[21] Appl. No.: 172,056

[22] Filed: Mar. 23, 1988

[51] Int. Cl.$^5$ .................. A01N 37/10; A01N 43/60
[52] U.S. Cl. ................................. 514/254; 514/544
[58] Field of Search ............................. 514/254, 544

[56] References Cited
PUBLICATIONS

Gottfried, N. S., Am. J. Hosp. Pharm. 19:310–314 (1962).
Fernandes et al., Antimicrobial Agents and Chemotherapy 29:201 (1986).
Barry et al., Antimicrobial Agents and Chemotherapy 29:40 (1986).
Stamm et al., Antimicrobial Agents and Chemotherapy 29:193 (1986).
United States Pharmacopeia XXI, p. 1151 (1985).
Material Safety Data Sheet (NIPA Laboratories, Inc., 11/26/85, 2 sheets, Krutzar).

Primary Examiner—Allen J. Robinson
Attorney, Agent, or Firm—Daniel R. Curry

[57] ABSTRACT

An antimicrobial composition containing quinolones and parabens provides surprising fungicidal and bactericidal activity when used in serum or protein-based in-vitro diagnostic kits. Also, a method of inhibiting the growth of bacteria and fungi in in-vitro diagnostic kits by adding the new antimicrobial composition to the kit components.

3 Claims, 6 Drawing Sheets

FIG. 6

ANTIMICROBIAL FOR IN-VITRO DIAGNOSTIC KITS

TECHNICAL FIELD

This invention relates to novel and potent antimicrobial compositions for in-vitro serum based diagnostic assay kits comprising a blend of quinolone and paraben. Also, this invention relates to a method of inhibiting microorganisms in in-vitro serum based diagnostic assay kits which comprises combining effective amounts of the new antimicrobial compositions with the kit components.

BACKGROUND

Many current diagnostic in-vitro assays are sold in kit form to the final user, who must use the purchased kit within a specified shelf life of the product. Many assay kits are used to assay serum or plasma for a particular component. Many kits have controls that contain human or bovine sera and reagents that are used during the assay to react with test serum or plasma.

Since kits are dated with a specific shelf life, the various components of the kit must be protected against microbial contamination for the shelf life through the use of preservatives or antimicrobials. Unfortunately, some well known preservatives cannot be used in certain diagnostic assay kits. For example, sodium azide cannot be used with horseradish peroxidase conjugates because it interferes with the heme group of the horseradish peroxidase. Gentamicin is ineffective against fungi. Thimerosal contains mercury which cannot be used in certain countries, such as Japan, because of its undesirable health and environmental effects.

Esters of p-hydroxybenzoic acid are known to be effective against both bacteria and fungi, but data suggests that in diagnostic assays, their efficacy may be blocked by serum proteins. These esters also have low solubility in aqueous systems, making formulating with them difficult. In particular, alkyl p-hydroxybenzoate esters, also known as parabens, have demonstrated antimicrobial properties. At low concentrations, parabens exhibit broad spectrum antimicrobial activity against gram positive and qram negative bacteria, and against fungi. Currently the parabens are used primarily in the food and cosmetic industries. See Gottfried, N.S., Alkyl p-Hydroxybenzoate Esters as Pharmaceutical Preservatives (A Review of the Parabens), Am. J. Hosp. Pharm. 19:310–314 (1962).

Substituted 4-oxo-1,4-dihydroquinoline-3-carboxylic acids and substituted 4-oxo-1,4-dihydro-1,8-naphthyridine-3-carboxylic acids, known as quinolones, are antibacterials that are used clinically as antibiotics, and are not known to be fungicidal or fungistatic. Aryl-fluoroquinolones, particularly ciprofloxacin, ofloxacin, enoxacin, norfloxacin, difloxacin and the quinolone commonly known as A-56620 have been evaluated for both in-vivo and in-vitro antibacterial activity. A-56620 is structurally similar to norfloxacin, except for a p-fluorophenyl substitution at position 1. All of the above aryl-fluoroquinolones exhibit various levels of antibacterial activity to aerobic bacteria. See, Fernandes, P. B. et al., In Vivo Evaluation of A-56619 (Difloxacin) and A-56620: New Aryl-Fluoroquinolones, Antimicrobial Agents and Chemotherapy 29:201 (1986); Barry, A. L. et al., In Vitro Evaluation of A-56619 and A-56620, Two New Quinolones, Antimicrobial Agents and Chemotherapy 29:40 (1986). However, when A-56620 and difloxacin were evaluated for antibacterial activity using a culture broth containing 50% serum, the potency of these quinolones decreased by an average of 4-fold for A-56620 and from 4- to 64-fold for difloxacin. Stamm, J.M. et al., In Vitro Evaluation of A-56619 (Difloxacin) and A-56620: New Aryl-Fluoroquinolones, Antimicrobial Aqents and Chemotherapy, 29:193 (1986).

Although both the aryl-fluoroquinolones and the parabens exhibit broad spectrum antimicrobial activity, the aryl-fluoroquinolones against bacteria and the parabens against bacteria and fungi, both show a loss of potency with serum based test systems.

An antimicrobial that is stable over the shelf life of the in-vitro diagnostic assay kit, that is effective in the presence of serum or plasma or other proteinaceous material, and which has broad spectrum antimicrobial activity against fungi and bacteria would minimize the problems currently associated with in-vitro diagnostic assay kits. A need also exists for a method of protecting these assay kits against microbial contamination.

BRIEF SUMMARY

It has now been discovered that an antimicrobial composition comprising an aryl-fluoroquinolone and a paraben has both fungicidal and bactericidal activity in serum based in vitro diagnostic assay kits. This new antimicrobial composition shows greater efficacy than does either of the components alone at twice the concentration.

A presently preferred antimicrobial composition according to the invention comprises aryl-fluoroquinolone at a concentration of from about 0.03 to about 10 micrograms/ml, more preferably about 5 micrograms/ml and paraben at a concentration of from about 0.01 to about 0 2% (w/v), more preferably about 0.1% (w/v).

Another preferred composition comprises the aryl-fluoroquinolone A-56620 at a concentration of about 5 micrograms/ml and a combination of ethyl-, methyl- and propyl-parabens at a concentration of about 0.1% (w/v).

Also described is a method of inhibiting bacteria and fungi in reagents and controls of serum based diagnostic kits which comprises adding to the reagents and controls an amount of the new antimicrobial composition effective to inhibit the growth of bacteria and fungi.

DISCLOSURE OF THE INVENTION

This invention relates to novel and potent antimicrobial agents for use in in-vitro diagnostic assays.

The antimicrobial agents employed in the invention comprise: (a) at least one compound selected from the group consisting of a class of compounds commonly known as "quinolones" having the general structure:

(I)

(II)

wherein R is selected from the group consisting of cyclopropyl, ethyl, 2-fluoroethyl, p fluorophenyl, and o,p-difluorophenyl; X is selected from the group consisting of CH, CF, CCl and N; Y is selected from the group consisting of O, S, and CH2; and Z is selected from the group consisting of piperazinyl, 4-methylpiperazin-l-yl, 3-methylpiperazin-l-yl, 3-aminopyrrolidin-l-yl, 2-methyl-4-aminopyrrolidin-l-yl, pyrrolyl and imidazolyl; or salts thereof; and (b) at least one compound selected from alkyl p-hydroxybenzoate esters having the general structure:

wherein R is selected from the group consisting of $CH_3$, $C_2H_5$, $C_3H_7$, $C_4H_9$, $C_7H_{15}$ and )$CH_2$; or salts thereof. Compositions comprisinq more than one quinolone compound and/or more than one paraben compound are also particularly useful.

In the quinolone compounds, the term "salts thereof" means the nontoxic acid addition alkaline earth metal salts of the compounds of I or II. These salts can be prepared in situ during the final isolation and purification of the compounds of I or II, or by separately reacting the base or acid functions with a suitable organic or inorganic acid or base, respectively. Representative acid addition salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, glucoheptonate, lactobionate, lauryl sulfate salts and the like. Representative alkali metal or alkaline earth metal salts include the sodium, calcium, potassium, magnesium salts, and the like.

In the alkyl p-hydroxybenzoate esters, the term "salts thereof" includes representative alkali metal or alkaline earth metal salts, including sodium, calcium, potassium, magnesium salts and the like.

The composition of the invention comprises an amount of the quinolone and of the paraben sufficient to obtain an antimicrobial effect when employed in a diagnostic reagent system. A preferred composition of the new antimicrobial combines the quinolone at a concentration of from about 0.03 to about 10 micrograms/ml and the paraben at a concentration of from about 0.01 to about 0.2% (w/v). This range allows for flexibility since not all quinolones have the same efficacy against bacteria and the various parabens have different solubilities. However, standard minimum inhibitory concentration (MIC) tests run on a number of quinolones show this range to be adequate for a variety of quinolones. Many of the non-salt forms of the parabens have a limit of solubility (defined as grams per 100 grams of water at 25 deg. C.) below 0.2% (w/v). Therefore, in a water based system, unless a salt of the paraben is used, the limits of solubility are soon reached. Heating the water while adding the nonionic paraben will put the paraben into solution. However, at the same time, heating may damage or destroy the proteins in the test assay.

A more preferred composition of the new preservative is the concentration of the quinolone at about 5 micrograms/ml and about 0.1% (w/v) of the paraben.

It has been surprisingly found that when an antibacterial quinolone, which is not fungicidal, and an antibacterial, antifungal paraben are combined and added to serum based diagnostic assay kit cortiponents, the new composition has a greater antimicrobial effect than does either component alone. This antimicrobial effect is seen when the concentration of each of the components is one-half that normally used when either the quinolone or the paraben is used as an antimicrobial alone.

Alkyl p-hydroxybenzoate esters and their salts are produced by Nipa Laboratories, Inc., under the name of Nipa Esters (®). In particular, a blend of three of these esters is known by the name Nipasept (®). Nipasept (®) is a combination of parabens which consists of approximately 65 to 70% (w/w) methyl p-hydroxybenzoate, approximately 15 to 20% (w/w) of ethyl p-hydroxybenzoate and approximately 10 to 15% (w/w) of propyl p-hydroxybenzoate, and has a solubility of 0.2% w/v in water.

The presently most preferred composition of the new antimicrobial is the quinolone A56620 which has a structure as (I) above and wherein R is p-fluorophenyl, X is CH and Z is piperazinyl at a concentration of about 5 micrograms/ml and Nipasept(®) at a concentration of about 0.1% (w/v). This composition has shown to be more effective in the serum based diagnostic kits than either the quinolone or paraben alone, even at twice the concentration, and also shows an unexpected increase in fungistatic and fungicidal efficacy. The increased antifungal effect is especially surprising since the quinolone is not an antifungal agent and the paraben is being used at one-half the concentration when tested alone.

Adding the new antimicrobial composition as described above to the reagents and controls of serum based conjugates used in diagnostic kits in effective amounts sufficient to inhibit the growth of bacteria and fungi is a method for preserving the usefulness of the kits by inhibiting the growth of bacteria and fungi.

The following examples illustrate the practice of the invention.

Example 1 relates to antimicrobial preservative effectiveness testing on three antimicrobial agents: A-56620, Nipasept, and the new antimicrobial combination of A-56620/Nipasept. The concentration of each component of the antimicrobial composition was one-half of that used for A-56620 and Nipasept alone. Thimerosal was used as a standard antimicrobial. Three different conjugate diluents were used as the assay diluent. A group of spore formers and fungi were the challenge organisms used. Example 2 relates to an antimicrobial preservative effectiveness test using the same antimicrobials as Example 1, but using only Conjugate C diluent and a group of bacteria as the challenge organisms. Example 3 relates to stability tests of the A56620-/Nipasept preservative in in-vitro diagnostic kits.

The examples which follow are for illustrative purposes only and are not intended in any way to limit the scope of the invention.

EXAMPLE 1

The four preservatives tested in this antimicrobial preservative effectiveness test were: A-56620 at 10 micrograms/ml (w/v), Nipasept at 0.2% (w/v), A-56620/Nipasept at 5 micrograms/ml (w/v) of A-56620 and 0.1%(w/v) of Nipasept, and thimerosal at 0.01% (w/v).

The three test conjugate diluents selected, based on their different salt and serum compositions, were:

Conjugate A 0.01 M Tris, pH 7.5
0.5% Calfskin Gelatin
2% Brij-35
1mM MgCl2
10% mannitol
Test Preservative
Distilled water q.s. to one liter

Conjugate B 0.1 M Tris, pH 7.4
15% Calf Serum
0.5 M NaCl
Test Preservative
Distilled water q.s. to one liter

Conjugate C 0.1 M Tris, pH 7.4
50% Calf Serum
3% Normal Mouse Serum
0.1M NaCl
Test Preservative
Distilled water q.s. to one liter USP recommended organisms, obtained from the American Type Culture Collection, and field isolates were used in this test. The challenge organism groups consisted of:
Group I—*A. niger, C. albicans, B. subtilis* and five mold field isolates.
Group III—Saline (negative control)

The antimicrobial preservative effectiveness test procedure used, well known to those skilled in the art, was the procedure described in the United States Pharmacopeia XXI, p. 1151 (1985), the disclosure of which is hereby incorporated by reference, modified as described below.

Each individual organism in the group was prepared from stock cultures, grown on suitable agar, and incubated at 30–35deg. C. for the standard length of time. Each microorganism was prepared as a standard inoculum in sterile saline, with a final concentration of $10^4$–$10^6$ CFU/ml. All microorganisms were combined into one standardized inoculum, identified as Group I.

Each conjugate or control was inoculated with the standardized inoculum, using the ratio equivalent of 0.10 ml of inoculum to 20 ml of conjugate or control. The inoculated conjugates and controls were incubated at 30–35 deg. C. for 14 days, and checked for growth on days 0, 7 and 14 through a standard plate count method using Tryptic Soy Agar in a pour plate. The percentage of microorganisms that survived were calculated. All results were reported relative to the saline controls.

Cidal activities were defined as 99.9% reduction (3 log) of microorganisms within 14 days. A preservative was determined to be effective if it showed cidal activity against bacteria and if it was static or cidal against fungi. Alternatively, a preservative was static, or showed no increase in total growth, if it showed less than a 3 log reduction in growth. A 90% reduction of microorganisms was shown as a 1 log kill and a 99% reduction of microorganisms was a 2 log kill.

Figure 1:
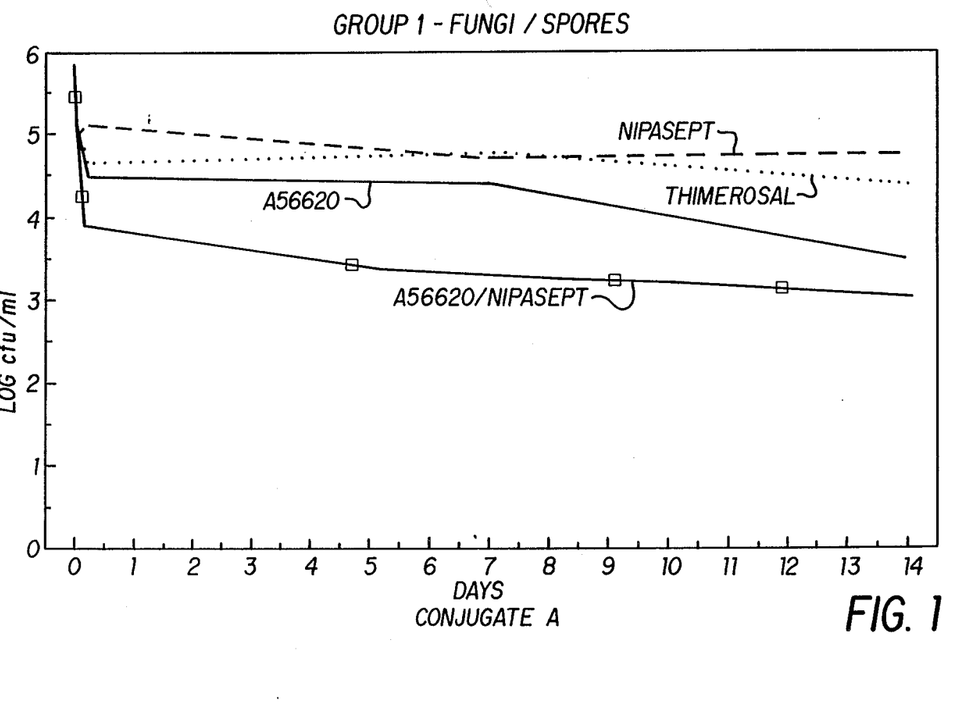
FIG. 1: A plot of log CFU/mL vs. days, using Group I organisms, conjugate A and A-56620, Nipasept, thimerosal and A-56620/Nipasept.
Figure 2:
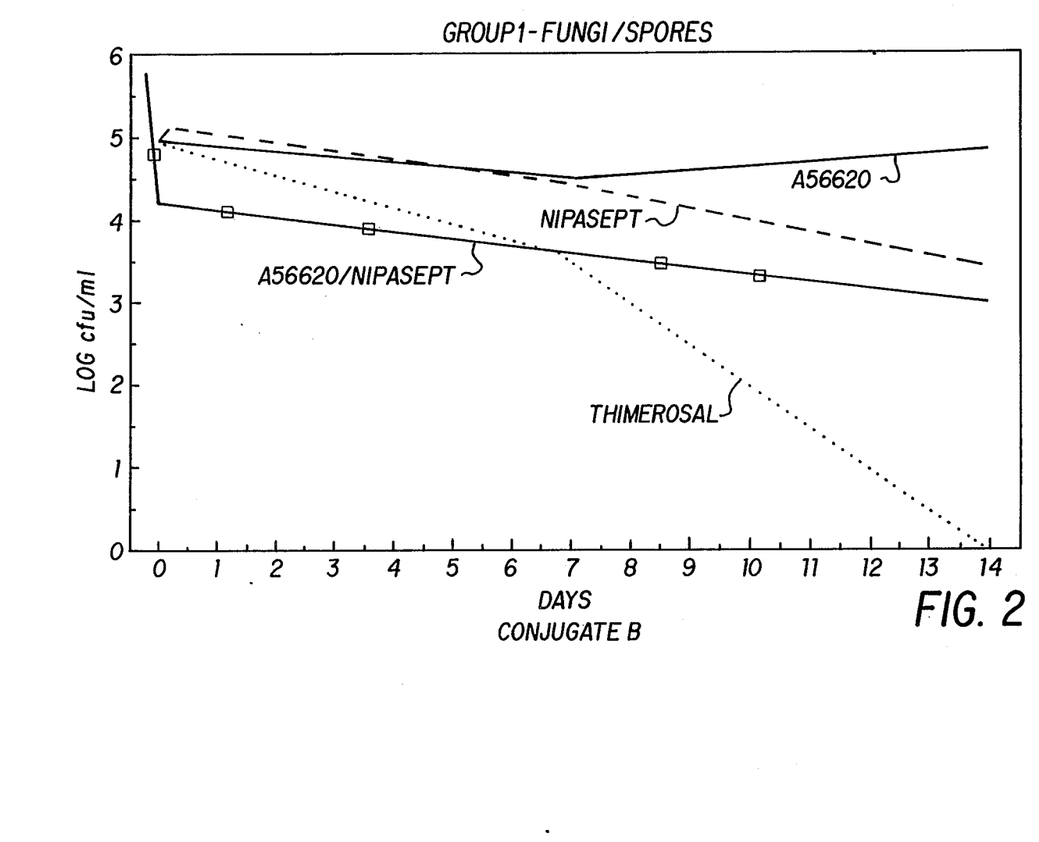
FIG. 2: A plot of log CFU/ml vs. days, using Group I organisms, conjugate B and A-56620, Nipasept, thimerosal and A-56620/Nipasept.
Figure 3:
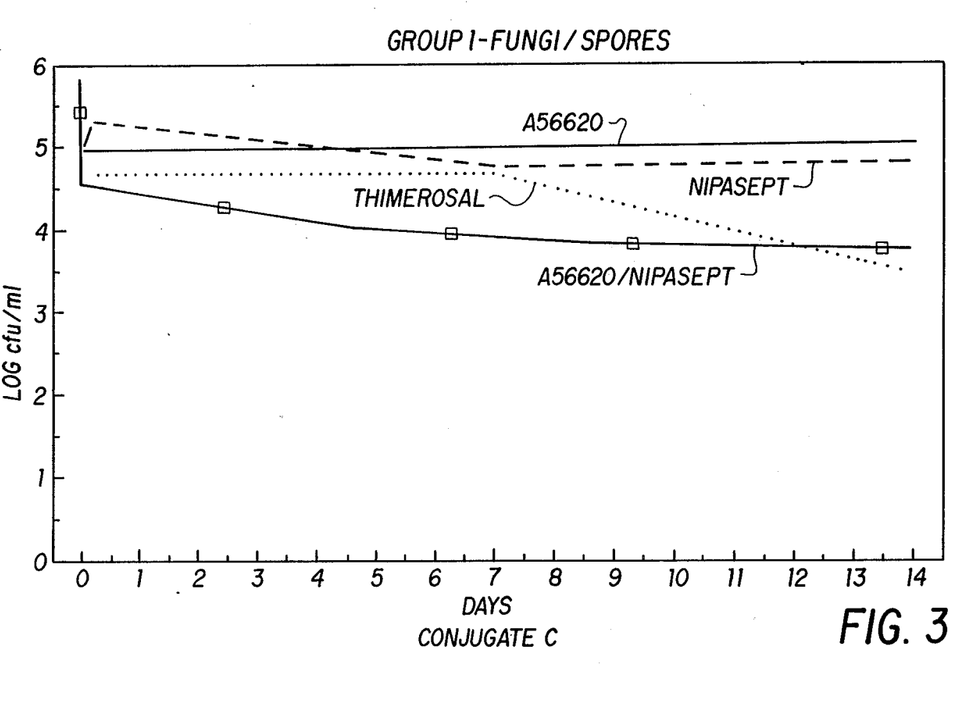
FIG. 3: A plot of log CFU/ml vs. days, using Group I organisms, conjugate C and A-56620, Nipasept, thimerosal and A-56620/Nipasept.

FIGS. 1, 2 and 3 demonstrate the antimicrobial activity of A-56620, Nipasept, thimerosal and A-56620/Nipasept against Group I organisms grown in conjugates A (FIG. 1), B (FIG. 2) and C (FIG. 3) for 14 days.

These results show that against Group I organisms, neither Nipasept or A-56620 alone are as effective as thimerosal nor the new preservative combination A-56620/Nipasept. The concentration of each of A-56620 and Nipasept in the new combination was only one-half that used when A-56620 or Nipasept were the sole antimicrobials.

In Conjugate A, A-56620 had a 1.5 log kill, approximately a 95% reduction in total microorganisms, and Nipasept had less than 0.5 log kill. With thimerosal as the preservative, there was a final approximately 0.5 log kill by day 14. Therefore, no fungicidal activity was shown by any of these preservatives, although fungistatic activity was shown by A56620. However, the new preservative combination showed fungicidal activity, defined as a 3 log kill or a 99.9% kill.

In Conjugate B, A-56620 had almost no reduction in total microorganisms over 14 days, Nipasept had a 1.5 log kill and thimerosal had a 5 log kill. The new preservative combination had a 3 log kill, or a 99.9% reduction in microorganisms. Again, the quinolone and the paraben were not fungicidal, whereas the new combination showed itself to be fungicidal.

In relation to Conjugates A and B, Conjugate C contained the greatest amount of serum, 50%, in its formulation. Here, neither A56620 nor Nipasept showed greater than a 0.5 log kill, and thimerosal had approximately a 1.5 log kill, while the new preservative had a 99.5% kill or a 2.5 log reduction in fungi.

Based on the above definition of fungicidal activity, only thimerosal in Conjugate B showed fungicidal activity. However, the new combination did exhibit fungistatic activity in Conjugates A and B, and showed a 2.5 log kill in Conjugate C, while A-56620 and Nipasept alone were either static or showed growth.

EXAMPLE 2

Figure 4:
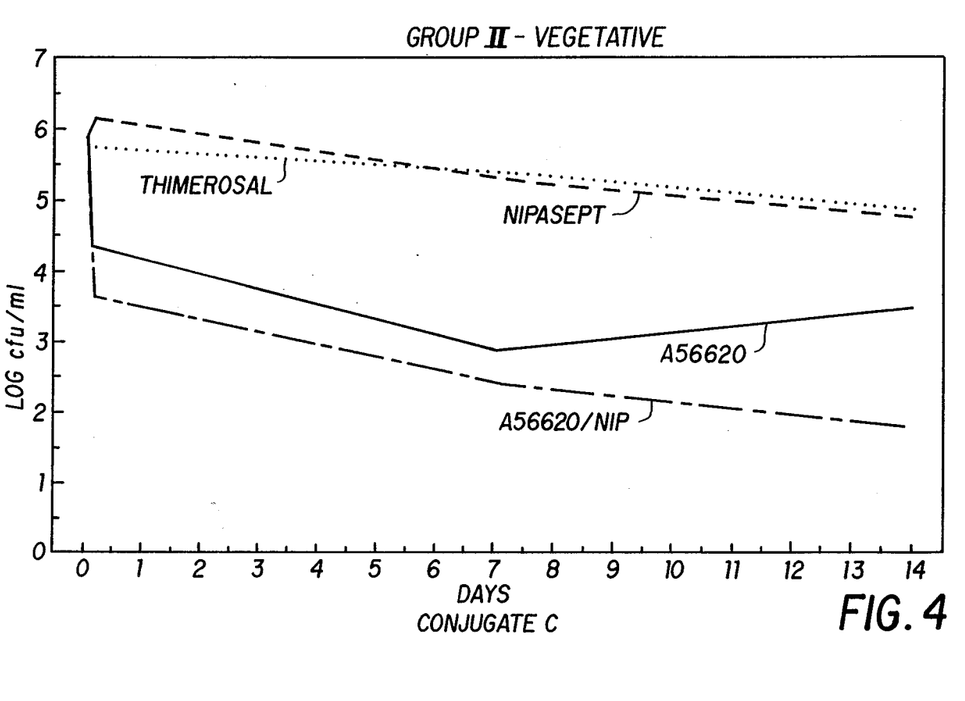
FIG. 4: A plot of log CFU/ml vs. days, using Group II organisms, conjugate C and a-56620, Nipasept, thimerosal and A-56620 /Nipasept.

Example 2 was performed in the same manner as Example 1, except that the organisms were those of Group II, which consisted of *E. coli, S. aureus* and *P. maltophilia*, and only Conjugate C was used. Conjugate C was chosen as the test medium because of its high level of serum. FIG. 4 demonstrates the antimicrobial activity of A-56620, Nipasept, thimerosal and A-56620/Nipasept against Group II organisms grown in Conjuqate C for 14 days.

The results of this experiment show that the new preservative A-56620/Nipasept is much more effective than any of the other preservatives tested, including thimerosal, in a heavy serum based solution such as Conjuqate C. A-56620 had an approximately 2.5 log kill, Nipasept and thimerosal had a log kill of about 1.5, and the new preservative combination had an approximately 4.25 log kill. In this example it is shown that the new preservative is a much more potent antibacterial than any of the other three preservatives, especially since each component of the new preservative is used at half the concentration of the individual ingredients when the individual ingredients were used as the sole antimicrobials. Since a preservative is defined as effective against bacteria only if it is cidal, only the new preservative composition fulfills this requirement.

EXAMPLE 3

In order to test the stability of the new preservative, it was tested in in-vitro diagnostic assay kits. The A-56620/Nipasept preservative was used in an Abbott Carcinoembryonic Antigen Monoclonal assay test kit. The kits contain low and high controls, which contained the new preservative, and which were tested for stability over four months. These controls consist of cell culture-derived carcinoembryonic antigen spiked into a buffer matrix with carrier protein, and A-56620/Nipasept at a concentration of A-56620 at 5 micrograms/ml and Nipasept at 0.1% (w/v).

All assay kit reagents were stored at 2-8 deg. C. and reference specimens at −20 deg. C. Sufficient reagents were removed each month and used in the appropriate enzyme immunoassay procedure for the detection of carcinoembryonic antigens. The potency of the reference specimens were used as the criteria to establish the validity of the enzyme immunoassay. A failure of any component of the kit, including the preservative, would have produced unacceptable results in the immunoassay.

Figure 5:
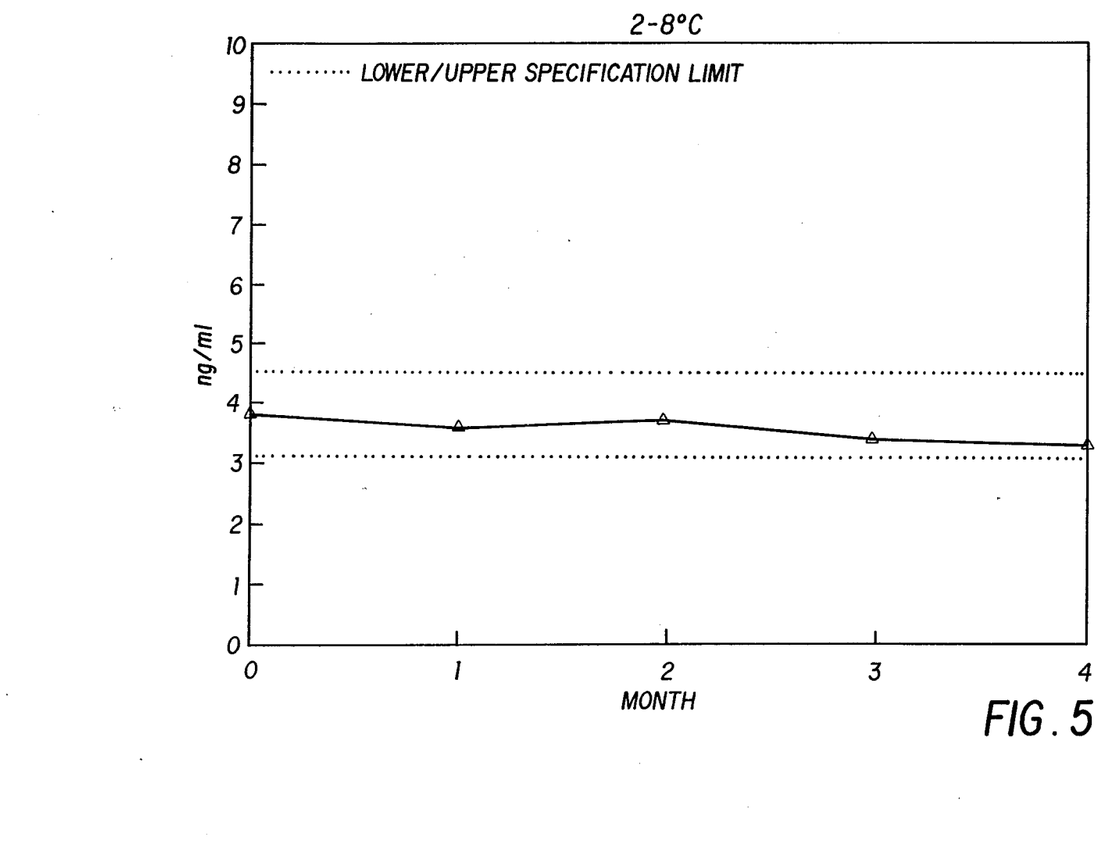
FIG. 5: A plot of the stability of the low control of an in-vitro diagnostic kit.

FIG. 5 shows the lower specification limit for the low control to be approximately 3.2 ng/ml and the upper specification limit to be approximately 4.6 ng/ml. The stability of the low control was maintained throughout the four month period.

Figure 6:
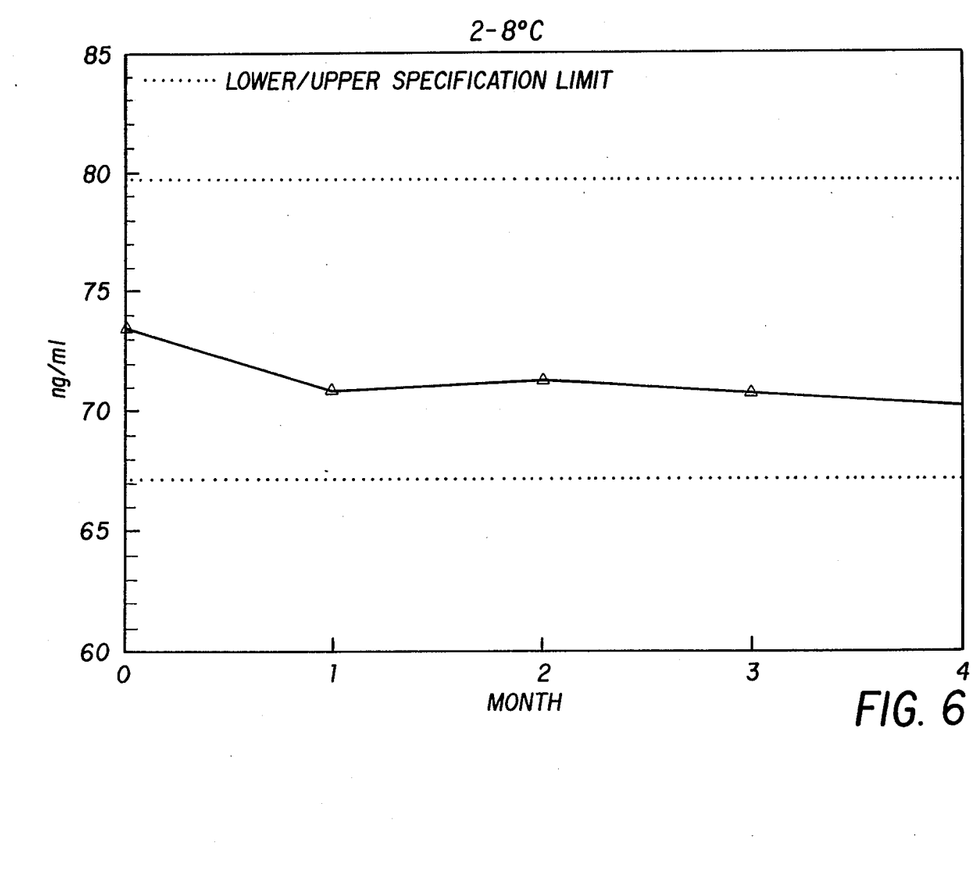
FIG. 6: A plot of the stability of the high control of an in-vitro diagnostic kit.

The lower and upper specification limits for the high control are approximately 67.1 ng/ml and 79.9 ng/ml, as shown in FIG. 6, and the high control also stayed within these boundaries during the four month period. If any component of the controls would have failed, the controls would have fallen outside of the upper or lower specification limits.

Therefore, the preservative, as well as the other components of the controls, were stable for a four month period.

These examples related to anti-microbial compositions comprising a quinolone and a paraben mixture. While the present invention has been described using specific methods and compositions, it is understood that variations and modifications will occur to those skilled in the art upon consideration of the present invention.

We claim:

1. An antimicrobial composition comprising a synergistic combination of: (a) an aryl-fluoroquinolone having the structure:

wherein R is p-fluorophenyl, X is CH and Z is piperazinyl and (b) a p-hydroxybenzoate ester blend comprising from about 65 to about 70% (w/w) methyl p-hydroxybenzoate, from about 15 to about 20% (w/w) of ethyl p-hydroxybenzoate and from about 10 to about 15% (w/w) of propyl p-hydroxybenzoate wherein the concentration of (a) is from about 0.03 micrograms/ml to about 10 micrograms/ml and the concentration of (b) is from about 0.01% (w/v) to about 0.2% (w/v)

2. The antimicrobial composition according to claim 1 comprising said aryl-fluoroquinolone at a concentration of about 5 micrograms/ml and said p-hydroxybenzoate ester blend at a concentration of about 0.1% (w/v).

3. A method of inhibiting bacteria and fungi in reagents and controls of serum based diagnostic kits, which method comprises adding to the reagents and controls an amount of said antimicrobial composition according to claim 1 effective to inhibit the growth of bacteria and fungi.

* * * * *